US008655449B2

(12) United States Patent
Haller et al.

(10) Patent No.: US 8,655,449 B2
(45) Date of Patent: Feb. 18, 2014

(54) MODULAR COCHLEAR IMPLANT SYSTEMS INCLUDING IMPLANTABLE SOUND PROCESSORS

(75) Inventors: Matthew I. Haller, Valley Village, CA (US); Leonid M. Litvak, Los Angeles, CA (US); Abhijit Kulkarni, Newbury Park, CA (US)

(73) Assignee: Advanced Bionics AG, Zug (CH)

( * ) Notice: Subject to any disclaimer, the term of this patent is extended or adjusted under 35 U.S.C. 154(b) by 976 days.

(21) Appl. No.: 12/696,275

(22) Filed: Jan. 29, 2010

(65) Prior Publication Data
US 2010/0198303 A1    Aug. 5, 2010

Related U.S. Application Data

(60) Provisional application No. 61/148,660, filed on Jan. 30, 2009.

(51) Int. Cl.
*A61N 1/372* (2006.01)
*A61N 1/378* (2006.01)
*A61N 1/36* (2006.01)

(52) U.S. Cl.
CPC .......... *A61N 1/36032* (2013.01); *A61N 1/3787* (2013.01); *A61N 1/372* (2013.01)
USPC .............................................. 607/57; 607/61

(58) Field of Classification Search
USPC .................................... 607/55–57, 60–61, 65
See application file for complete search history.

(56) References Cited

U.S. PATENT DOCUMENTS

| 6,067,474 | A * | 5/2000 | Schulman et al. | 607/57 |
| 6,272,382 | B1 * | 8/2001 | Faltys et al. | 607/57 |
| 6,308,101 | B1 | 10/2001 | Faltys et al. | |
| 7,039,466 | B1 | 5/2006 | Harrison et al. | |
| 2006/0265061 | A1 | 11/2006 | Kwon et al. | |
| 2009/0157143 | A1 | 6/2009 | Edler et al. | |

FOREIGN PATENT DOCUMENTS

DE    102005049507    3/2007

OTHER PUBLICATIONS

International Search Report & Written Opinion received in PCT Patent Application No. PCT/US10/22634 dated Apr. 12, 2010.

\* cited by examiner

*Primary Examiner* — Carl H Layno
*Assistant Examiner* — Jessica Sarcione
(74) *Attorney, Agent, or Firm* — ALG Intellectual Property, LLC

(57) ABSTRACT

Exemplary cochlear implant systems include an implantable head module configured to be implanted within a head of a patient. The implantable head module includes a cochlear stimulator configured to be coupled to an electrode lead, the electrode lead including one or more electrodes configured to be in communication with one or more stimulation sites within the patient. The implantable head module also includes a signal receiver configured to receive a telemetry signal representative of an audio signal from a signal transmitter located external to the patient, a sound processor configured to process the telemetry signal and direct the cochlear stimulator to generate and apply electrical stimulation representative of the audio signal to the one or more stimulation sites via the electrode lead, and a power receiver configured to receive power for operating the implantable head module from a power transmitter located external to the patient.

14 Claims, 8 Drawing Sheets

MODULAR COCHLEAR IMPLANT SYSTEMS INCLUDING IMPLANTABLE SOUND PROCESSORS

RELATED APPLICATIONS

The present application claims priority under 35 U.S.C. §119(e) to U.S. Provisional Patent Application No. 61/148,660 by Matthew I. Haller et al., filed on Jan. 30, 2009, and entitled "MODULAR COCHLEAR IMPLANT SYSTEMS INCLUDING IMPLANTABLE SOUND PROCESSORS," the contents of which are hereby incorporated by reference in their entirety.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems. To overcome sensorineural hearing loss, numerous cochlear implant systems, or cochlear prosthesis, have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

Cochlear implant systems typically include a cochlear stimulator that is implanted beneath the scalp of a patient. An external control assembly located external to the patient's scalp is typically used to control and adjust various operational parameters of the implanted cochlear stimulator. An inductive link is used to transmit telemetry signals from the external control assembly to the implanted cochlear stimulator. In a conventional cochlear implant system, the external control assembly typically includes sound processing circuitry as well a battery that is used to power the implanted cochlear stimulator. Power is typically transferred through the scalp to the implanted cochlear stimulator via the inductive link. The external control assembly is often housed within a behind-the-ear unit and/or within a carrying case that can be attached to clothing worn by the patient.

One drawback associated with conventional cochlear implant systems is that their external control assemblies are powered by batteries, which are typically large, bulky, and relatively heavy due to the fact they must be sufficiently large to provide power for extended periods of time. Additionally, a conventional cochlear implant system is typically limited to a specific physical configuration, particularly with respect to the implanted components. Once a cochlear implant patient has been fitted with a cochlear implant system, the patient typically has to have the system surgically removed in order to change its physical configuration. Such procedures are invasive, costly, and undesirable.

SUMMARY

Exemplary cochlear implant systems include an implantable head module configured to be implanted within a head of a patient. The implantable head module includes a cochlear stimulator configured to be coupled to an electrode lead, the electrode lead including one or more electrodes configured to be in communication with one or more stimulation sites within the patient. The implantable head module also includes a signal receiver configured to receive a telemetry signal representative of an audio signal from a signal transmitter located external to the patient. The implantable head module additionally includes a sound processor configured to process the telemetry signal and direct the cochlear stimulator to generate and apply electrical stimulation representative of the audio signal to the one or more stimulation sites via the electrode lead. The implantable head module also includes a power receiver configured to receive power for operating the implantable head module from a power transmitter located external to the patient.

Exemplary cochlear implant systems include an implantable head module configured to be implanted within a head of a patient, the implantable head module including a cochlear stimulator configured to be coupled to an electrode lead, the electrode lead including one or more electrodes configured to be in communication with one or more stimulation sites within the patient. The implantable head module also includes a signal receiver configured to receive a telemetry signal representative of an audio signal from a signal transmitter located external to the patient. The implantable head module additionally includes a sound processor configured to process the telemetry signal and direct the cochlear stimulator to generate and apply electrical stimulation representative of the audio signal to the one or more stimulation sites via the electrode lead. The cochlear implant system further includes an implantable power module communicatively coupled to the implantable head module, the implantable power module being configured to produce power for operating the implantable head module.

Exemplary cochlear implant systems include an implantable head module configured to be implanted within a head of a patient, the implantable head module including a cochlear stimulator configured to be coupled to an electrode lead, the electrode lead including one or more electrodes configured to be in communication with one or more stimulation sites within the patient. The implantable head module also includes a signal receiver configured to receive a telemetry signal representative of an audio signal from a signal transmitter located external to the patient. Additionally, the implantable head module includes a sound processor configured to process the telemetry signal and direct the cochlear stimulator to generate and apply electrical stimulation representative of the audio signal to the one or more stimulation sites via the electrode lead. The implantable head module further includes a power receiver configured to receive power for operating the implantable head module from a power transmitter located external to the patient. The implantable head module also includes a power input port configured to receive power for operating the implantable head module from an implantable power module. The implantable head module is selectively configured to operate using power received by at least one of the power receiver and the power input port.

Exemplary implantable head modules configured to be implanted within a head of a patient include a cochlear stimulator configured to be coupled to an electrode lead, the electrode lead including one or more electrodes configured to be in communication with one or more stimulation sites within the patient. The implantable head module also includes a signal receiver configured to receive a telemetry signal representative of a first audio signal from a signal transmitter located external to the patient. The implantable head module additionally includes an audio input port configured to receive an electrical signal representative of a second audio signal from an implantable microphone. The implantable head module further includes a sound processor selectively configured to process at least one of the telemetry signal and the electrical signal, the sound processor being selectively configured to direct the cochlear stimulator to generate and apply electrical stimulation representative of at least one of the first audio signal and the second audio signal to the one or more stimulation sites via the electrode lead.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Cochlear implant systems including an implantable head module configured to be implanted within a head of a patient are described herein. The implantable head module may include a cochlear stimulator configured to be coupled to an electrode lead, the electrode lead including one or more electrodes configured to be in communication with one or more stimulation sites within the patient. The implantable head module may also include a signal receiver configured to receive a telemetry signal representative of an audio signal from a signal transmitter located external to the patient. The implantable head module may additionally include a sound processor configured to process the telemetry signal and direct the cochlear stimulator to generate and apply electrical stimulation representative of the audio signal to the one or more stimulation sites via the electrode lead. The implantable head module may also include a power receiver configured to receive power for operating the implantable head module from a power transmitter located external to the patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one example" or "an example" means that a particular feature, structure, or characteristic described in connection with the example is included in at least one example. The appearance of the phrase "in one example" in various places in the specification are not necessarily all referring to the same example.

Figure 1:
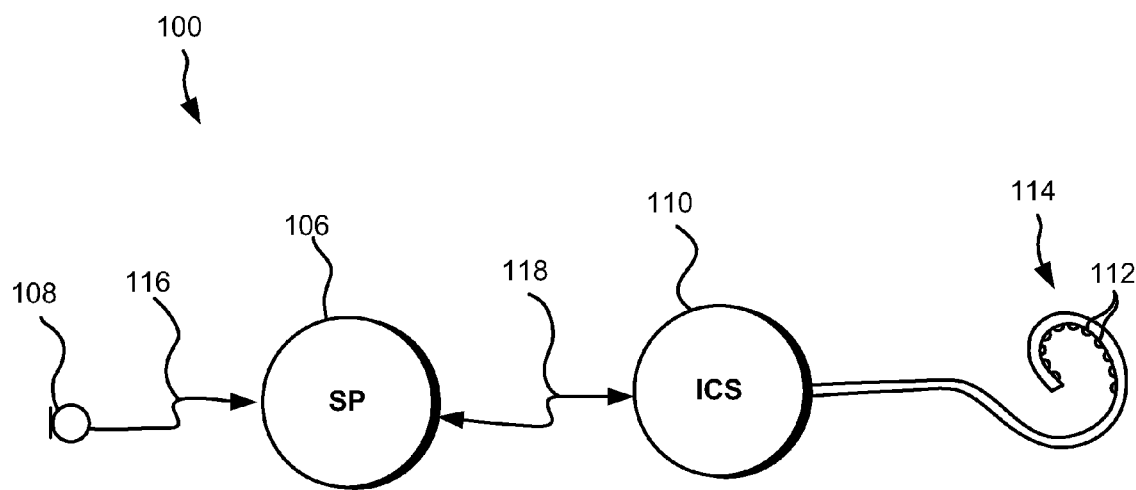
FIG. 1 illustrates an exemplary cochlear implant system according to principles described herein.

FIG. 1 illustrates an exemplary cochlear implant system 100. Cochlear implant system 100 may include, but is not limited to, a sound processor 106, a microphone 108, an implantable cochlear stimulator 110, a number of electrodes 112 disposed on an electrode lead 114, and/or additional circuitry as best serves a particular application. Each of these components will be described in more detail below.

The microphone 108 of FIG. 1 is configured to sense audio signals and convert the sensed signals to corresponding electrical signals. In some examples, the audio signal may include speech. The audio signal may additionally or alternatively include music, noise, and/or other sounds. The electrical signals are transmitted from the microphone 108 to the sound processor 106 via a communication link 116, which may include a telemetry link, a wire, and/or any other type of communication link 116 as may serve a particular application. Alternatively, the microphone 108 may be connected directly to, or integrated with, the sound processor 106.

The sound processor 106 is configured to process the converted audio signals in accordance with a selected sound processing strategy to generate appropriate stimulation parameters for controlling the implantable cochlear stimulator 110. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 110. The sound processor 106 and implantable cochlear stimulator 110 may be communicatively coupled via a suitable data or communication link 118. It will be understood that the data communication link 118 may include a bi-directional communication link and/or one or more dedicated uni-directional communication links.

The electrode lead 114 shown in FIG. 1 is configured to be inserted within a duct of a cochlea. As shown in FIG. 1, the electrode lead 114 includes a multiplicity of electrodes 112, e.g., sixteen electrodes, spaced along its length. It will be understood, however, that any number of electrodes 112 may be disposed on the electrode lead 114. Electronic circuitry within the implantable cochlear stimulator 110 is configured to generate and apply electrical stimulation to one or more stimulation sites within the cochlea via selected stimulation channels (i.e., pairs or groups of the individual electrodes 112) in accordance with a specified stimulation strategy defined by the sound processor 106. Hence, as will be described in more detail below, one or more electrode leads 114 with one or more electrodes 112 disposed thereon may be implanted within a patient such that the electrodes 112 are in communication with one or more stimulation sites within the patient. As used herein, the term "in communication with" refers to the electrodes 112 being adjacent to, in the general vicinity of, in close proximity to, directly next to, or directly on the stimulation site.

One or more components of cochlear implant system 100 may be implanted within a patient's body while one or more components of cochlear implant system 100 may be located external to the patient. For example, the sound processor 106, implantable cochlear stimulator 110, and/or electrode lead 114 may all be implanted within a patient's body while the microphone 108 may be located external to the patient. The microphone 108 may alternatively be implanted within the patient's body, as will be described in more detail below.

In some examples, as will be described in more detail below, the cochlear implant system 100 include at least one implantable induction coil and at least one induction coil configured to be located external to the patient that are configured to transmit and receive power and/or telemetry signals via one or more communication links. The power signals may be used to provide power to one or more components of cochlear implant system 100. The telemetry signals may include signals representative of audio signals sensed by microphone 108, one or more control signals, and/or any other type of signal as may serve a particular application.

Figure 2:
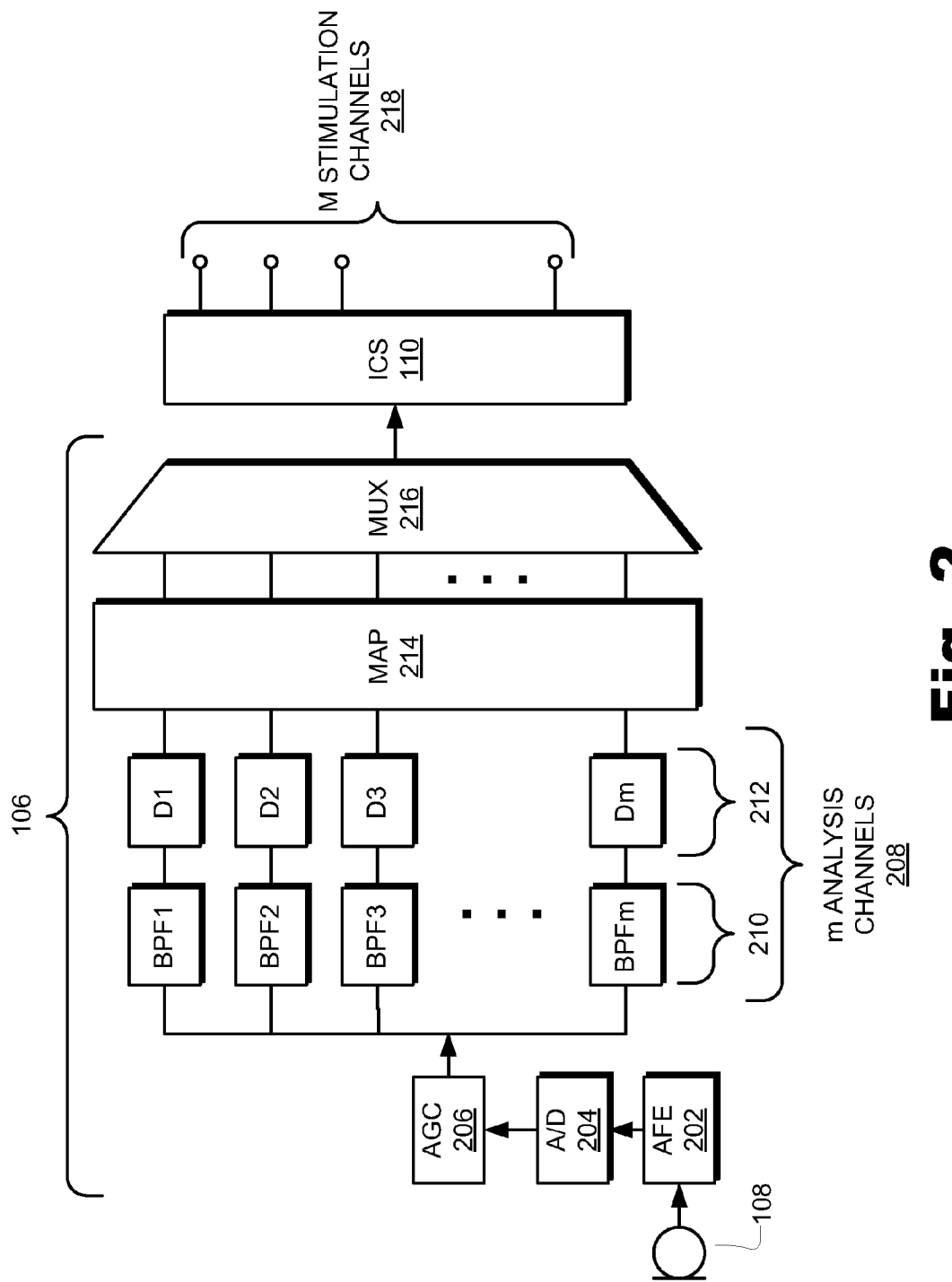
FIG. 2 is a functional block diagram of an exemplary sound processor and implantable cochlear stimulator according to principles described herein.

FIG. 2 is a functional block diagram of an exemplary sound processor 106 and implantable cochlear stimulator 110. The functions shown in FIG. 2 are merely representative of the many different functions that may be performed by the sound processor 106 and/or the implantable cochlear stimulator 110.

As shown in FIG. 2, the microphone 108 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) function 206.

After appropriate automatic gain control, the digital signal is then processed in one of a number of digital signal processing or analysis channels 208. For example, the sound processor 106 may include, but is not limited to, eight analysis channels 208. Each analysis channel 208 may respond to a different frequency band of the sensed audio signal due to a series of band pass filters 210.

As shown in FIG. 2, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include a rectification circuit followed by an integrator circuit.

After energy detection, the signals within each of the m analysis channels 208 are forwarded to a mapping stage 214. The mapping stage 214 is configured to map the signals in each of the m analysis channels 208 to one or more of M stimulation channels 218. In other words, the information contained in the m analysis channels 208 is used to define the electrical stimulation pulses that are applied to the patient by the implantable cochlear stimulator 110 via the M stimulation channels 218. As mentioned previously, pairs or groups of individual electrodes 112 may make up the M stimulation channels 218.

In some examples, the mapped signals are serialized by a multiplexer 216 and transmitted to the implantable cochlear stimulator 110. The implantable cochlear stimulator 110 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue (e.g., auditory nerve tissue 306 shown in FIG. 3).

Figure 3:
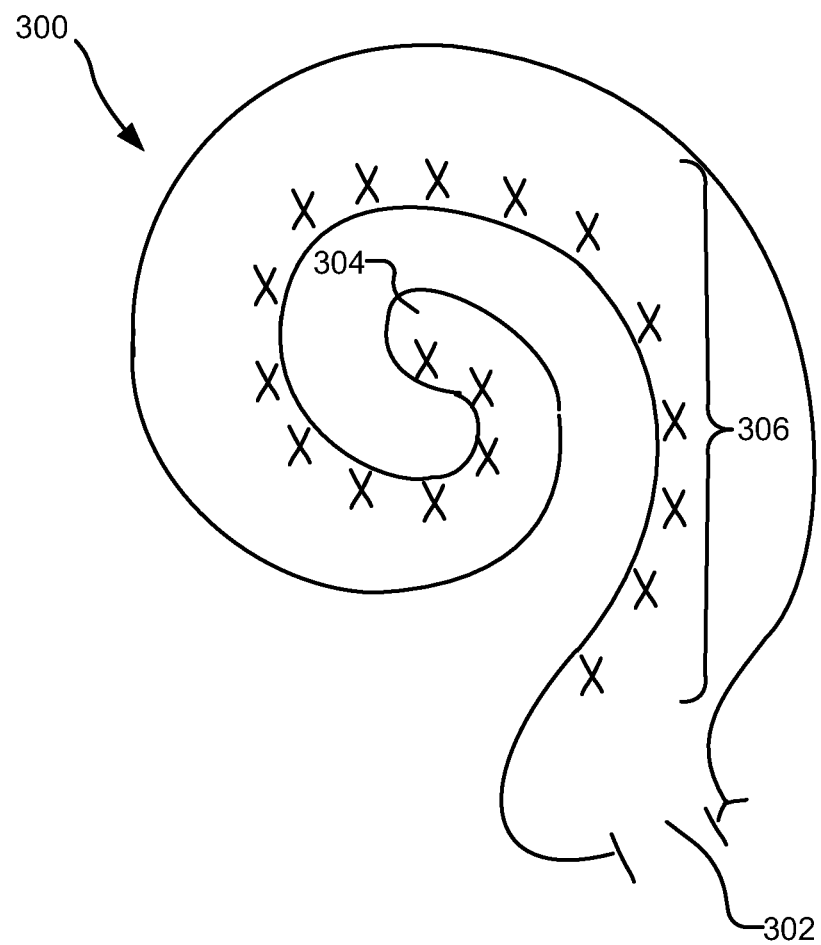
FIG. 3 illustrates a schematic structure of the human cochlea highlighting elements according to principles described herein.

FIG. 3 illustrates a schematic structure of the human cochlea 300. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. A cochlear prosthesis may therefore be implanted within a patient with sensorineural hearing loss and configured to apply electrical stimulation to different locations within the cochlea 300 to provide the sensation of hearing. For example, the electrode lead 114 may be disposed within the cochlea 300 such that the electrodes 112 are in communication with auditory nerve tissue 306 within the cochlea 300. Electrical stimulation may be applied by the electrodes 112 to the auditory nerve tissue 306.

FIGS. 4-8 illustrate exemplary modular configurations of cochlear implant system 100 that may be used in accordance with present systems and methods. The modular configurations shown in FIGS. 4-8 are merely illustrative of the many different cochlear implant system configurations that may be used in accordance with the present systems and methods. Additional or alternative components and/or configurations of cochlear implant system 100 may be used as may serve a particular application.

As will be described in more detail below, the modular configurations shown in FIGS. 4-8 each include various configurations obtainable with an implantable head module that may include an implantable sound processor 106, an implantable cochlear stimulator 110, multiple inputs configured to receive audio signals, and/or multiple inputs configured to receive power. The various modular configurations may enable a patient to be fitted with a particular configuration, while allowing for different configurations to be selected by the patient at a later time. Accordingly, a cochlear implant system 100 may be customized to suit needs and preferences of a particular patient. To illustrate, a relatively young child may be fitted with one of the modular configurations of a cochlear implant system 100 described herein in which portions of the system 100, such as the microphone and/or battery, are worn externally. After the child has matured into an adolescent or adult, certain components of the cochlear implant system 100 may be replaced such that the system 100 becomes a substantially or fully implantable system.

Figure 4:
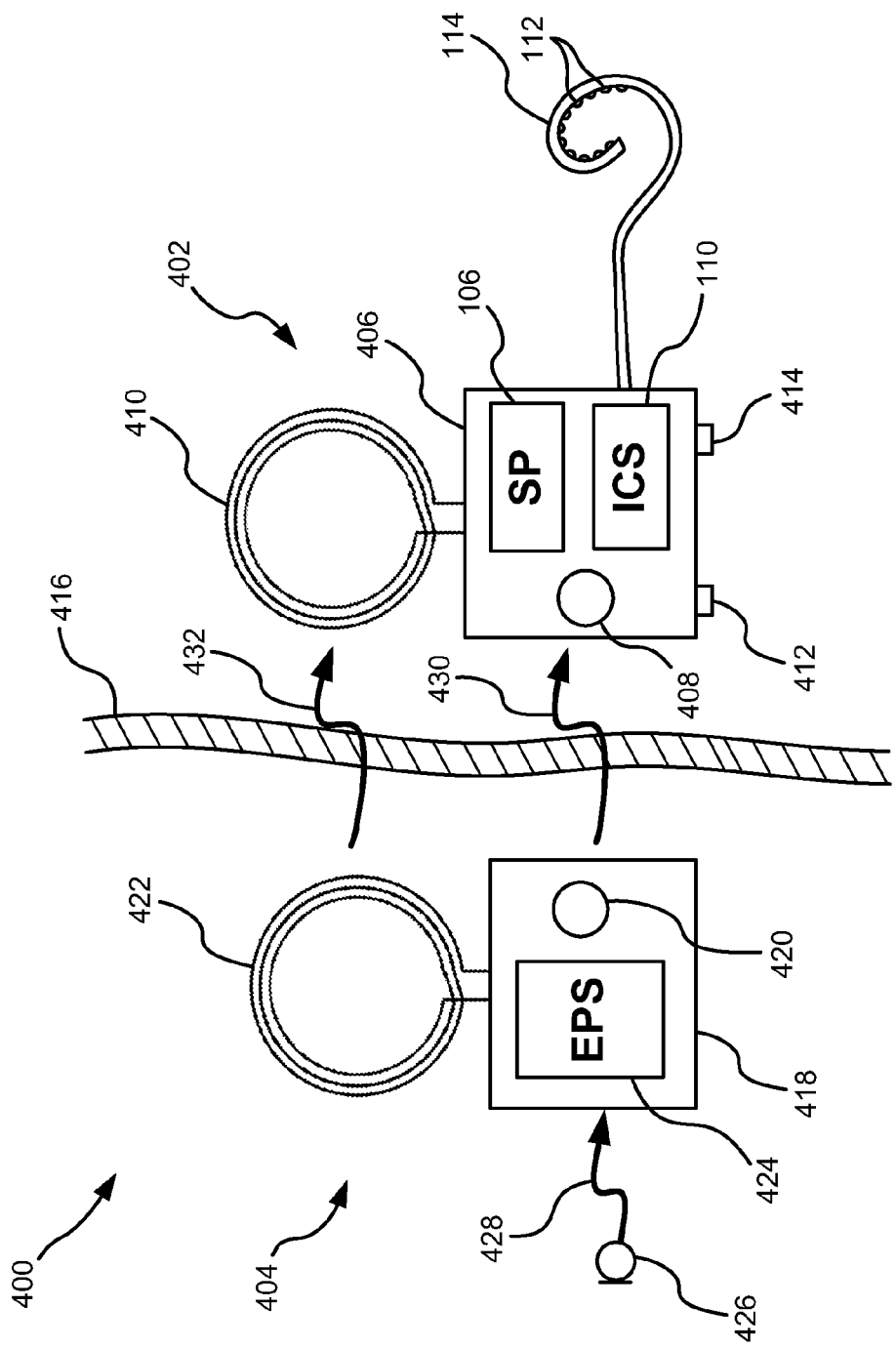
FIG. 4 illustrates an exemplary configuration of a cochlear implant system according to principles described herein.

FIG. 4 illustrates an exemplary modular configuration 400 of cochlear implant system 100 that may be used to apply electrical stimulation to one or more stimulation sites within the cochlea 300. As shown in FIG. 4, the configuration 400 may include an implantable head module 402 configured to be implanted within the head of a patient and an external head module 404 configured to be positioned external to the patient. As shown in FIG. 4, the sound processor 106 and implantable cochlear stimulator 110 are both included within the implantable head module 402. By including the sound processor 106 in the implantable head module 402 as opposed to having it positioned external to the patient, the size and/or weight of components of the cochlear implant system 100 mounted externally on the patient may be reduced.

In some examples, the implantable head module 402 may include a housing 406 configured to hermetically enclose at least the sound processor 106 and the implantable cochlear stimulator 110. The housing 406 may include, but is not limited to, a hermetic encasing configured to prevent entry therein of bodily fluids and may be made out of any suitable material including, but not limited to, metal, metal alloys, ceramics, plastics, polymers, and/or combinations thereof. For example, the housing 406 may be made out of titanium.

As shown in FIG. 4, the electrode lead 114 may be connected to the housing 406 and/or may extend into an interior portion of the housing 406 such that the electrode lead 114 is communicatively coupled to the implantable cochlear stimulator 110. In this manner, electrical stimulation generated by the implantable cochlear stimulator 110 may be applied to one or more stimulation sites within the patient.

The implantable head module 402 may also include a signal receiver 408 configured to receive one or more telemetry signals transmitted thereto by the external head module 404. The signal receiver 408 may include an implantable radio-frequency (RF) coil configured to receive and/or transmit RF telemetry signals or any other type of coil or receiver as may serve a particular application.

Signal receiver 408 may be located at least partially within the housing 406, as illustrated in FIG. 4. In some alternative embodiments, the signal receiver 408 may be located external to the housing 406. In some examples, the signal receiver 408 may be communicatively coupled to the sound processor 106 such that the signal receiver 408 may transfer received telemetry signals thereto. In some examples, the signal receiver 408 may additionally or alternatively receive power signals transmitted from a power supply located external to the patient.

In some embodiments, the implantable head module 402 may additionally include a power receiver 410 configured to receive power from a power supply located external to the patient and/or a power supply implanted at another location within the patient. The power receiver 410 may include any suitable component(s) configured to receive power from an externally located power supply.

For example, the power receiver 410 may include an implantable coil having a relatively high Q factor (i.e., quality factor). In this manner, the implantable power receiver 410 may receive energy over a relatively narrow frequency band, thus enabling power to be transferred from a power source to the power receiver 410 in a relatively efficient manner. While power receiver 410 includes a high-Q coil in the examples given herein, it will be recognized that power receiver 410 may alternatively include any other component configured to receive power as may serve a particular application.

In some examples, as shown in FIG. 4, the power receiver 410 may be disposed at least partially outside of housing 406. Additionally, the power receiver 410 may be at least partially encased in a protective coating or housing that is distinct from housing 406. For example, the power receiver 410 may be encased in a polymer, such as epoxy, to hermetically seal and protect the power receiver 410 from body fluids. In some alternative examples, the power receiver 410 may be disposed at least partially within housing 406.

The implantable head module 402 may additionally or alternatively include an audio input port 412 and/or a power input port 414. The audio input port 412 and the power input port 414 may be coupled to or otherwise a part of housing 406. For example, as shown in FIG. 4, the audio input port 412 and/or the power input port 414 may be coupled to and at least partially protrude from housing 406.

Audio input port 412 may be configured to receive an electrical signal representative of an audio signal from a microphone, such as an implantable microphone configured to be implanted within the patient. For example, the audio input port 412 may be configured to be electrically connected to a wire extending from an implantable microphone. An exemplary implantable microphone will be described in more detail below with reference to FIG. 7.

Power input port 414 may be configured to receive power from a power supply, such as an implantable power supply implanted within the patient, as discussed in more detail below with reference to FIG. 5. For example, the power input port 414 may be configured to be electrically connected to a wire or cable extending from an implantable power supply. In some examples, both the audio input port 412 and the power input port 414 may be sealed when they are not utilized to prevent body fluid from entering the ports and/or housing 406.

The audio input port 412 and the power input port 414 may enable patients to update the configuration of the cochlear implant system 100 to suit their needs and preferences at different times. For example, it may be decided to only initially implant the implantable head module 402 shown in FIG. 4 into a patient, and to forego implantation of a microphone or a power supply. Accordingly, an external power source and an external microphone may be configured to supply power and data representative of audio signals to the implantable head module 402. The patient may later desire to be implanted with an implantable microphone and/or an implantable power supply to replace the external microphone and/or the external power source. Without altering or replacing the implantable head module 402 already implanted within the patient, a doctor may implant an implantable microphone and/or an implantable power source within the patient. The doctor may then connect the implantable microphone and/or the implantable power source to the audio input port 412 and/or the power input port 414, respectively.

The external head module 404 shown in FIG. 4 may include a housing 418 configured to enclose one or more components of cochlear implant system 100 therein. The external head module 404 may be configured to be worn externally by a patient in any suitable manner. For example, the external head module 404 may be shaped such that it can be secured over and/or behind an ear of the patient. In some examples, the external head module 404 may be releasably secured to the head of the patient using a retention magnet or any other suitable retention means.

The external head module 404 may include a signal transmitter 420 configured to transmit one or more telemetry signals to the implantable head module 402 via telemetry link 430. The signal transmitter 420 may include an RF coil configured to transmit and/or receive RF telemetry signals or any other type of coil or transmitter as may serve a particular application. In some embodiments, the signal transmitter 420 may be disposed within housing 418. Alternatively, the signal transmitter 420 may be disposed outside of the external housing 418.

The external head module 404 may additionally include an external power supply ("EPS") 424 configured to provide power via a power transmitter 420 to one or more components within the implantable head unit 402. The external power supply 424 may be disposed within housing 418, as shown in FIG. 4, and electrically coupled to the power transmitter 422. The external power supply 424 may include any suitable type of power supply, including, for example, one or more rechargeable and/or replaceable batteries.

As shown in FIG. 4, the power transmitter 422 may be located at least partially outside housing 418. In some examples, the power transmitter 422 may include a high-Q coil configured to transmit power generated by the power supply 424 through the skin to the implanted power receiver 410 via power link 432. In such instances, the power transmitter 422 may be disposed within an external headpiece having a retention magnet configured to position the power transmitter 422 on the patient's head at a location substantially adjacent to power receiver 410. Power transmitter 422 may alternatively include any other component configured to transmit power to the implantable power receiver 410 as may serve a particular application.

In some examples wherein the power transmitter 422 and power receiver 410 are high-Q coils, power may be transferred therebetween by passing alternating current through power transmitter 422. The current causes an electro-magnetic field to surround the power transmitter 422, which in turn causes a current to be generated in the power receiver 410. The current generated in the power receiver 410 may then be transferred to one or more components of the implantable head module 402.

In some examples, a microphone 426 located external to the patient may be communicatively coupled to one or more components within the external head module 404 via a communication link 428. For example, the external microphone 426 may be communicatively coupled to the signal transmitter 420, which may be configured to transmit telemetry signals representative of audio signals detected by the external microphone 426 through the skin to the implanted signal receiver 408 via communication link 430.

In some examples, the external microphone 426 may be included within or otherwise integrated into the external head module 404. Alternatively, the external microphone 426 may be configured to wirelessly transmit telemetry detected audio signals to signal transmitter 420 located within external head module 404 and/or directly to signal receiver 408 located within implantable head module 402. In this manner, the external microphone 426 may be disposed at least partially within the ear canal or some other suitable location while the external head module 404 may be positioned in a more convenient location for communicating with implantable head module 402.

Figure 5:
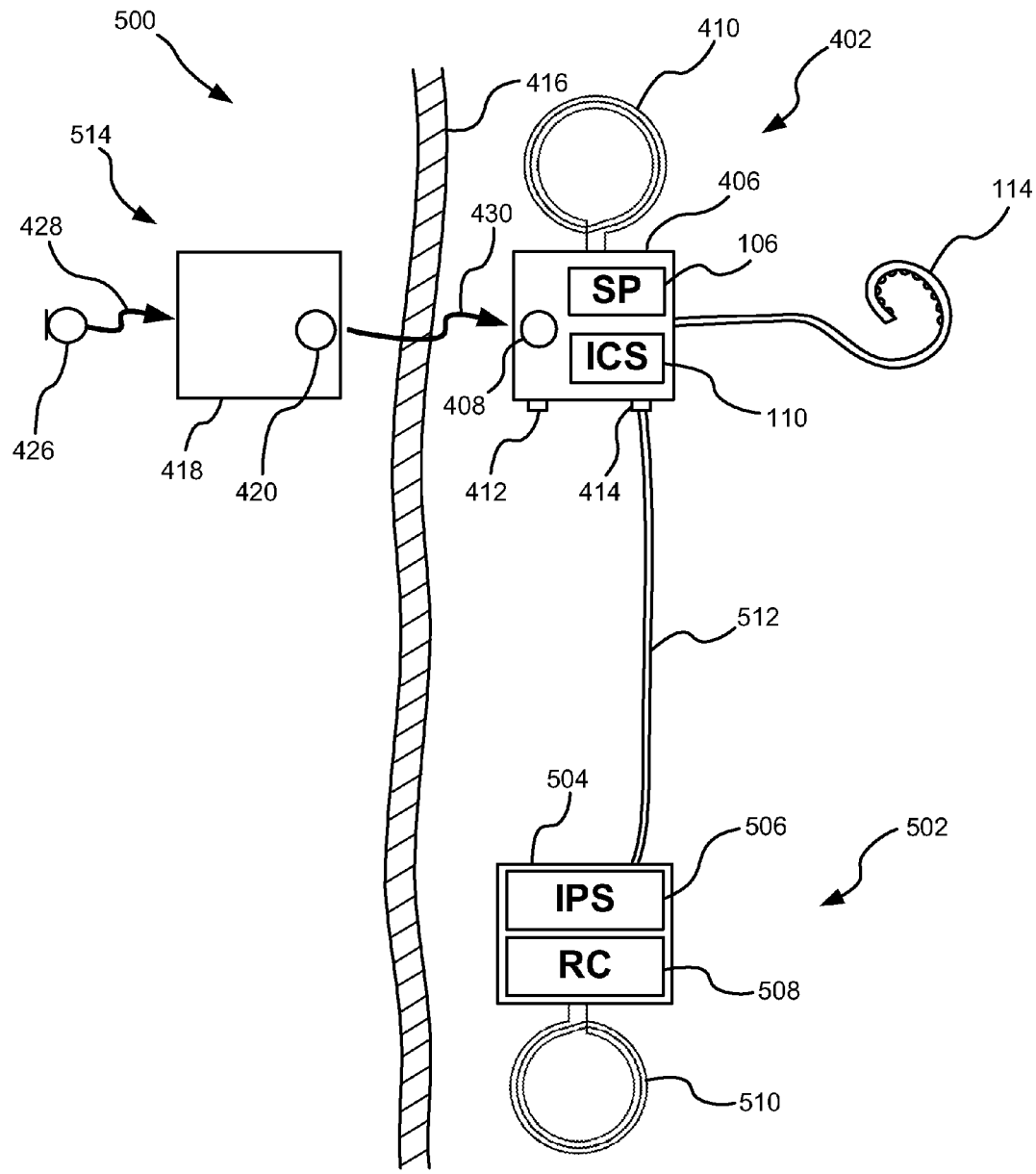
FIG. 5 illustrates an exemplary configuration of a cochlear implant system according to principles described herein.

FIG. 5 illustrates another exemplary modular configuration 500 of cochlear implant system 100 that may be used to apply electrical stimulation to one or more stimulation sites within the cochlea 300. The configuration 500 shown in FIG. 5 may include an implantable power module 502 configured to supply power to the implantable head module 402. To this end, the implantable power module 502 may include an implantable power supply 506, recharge circuitry 508, a power receiver 510, and/or any other component as may serve a particular application.

The power module 502 may be implanted within any suitable region within the patient. For example, the power module 502 may be implanted within a thoracic region of the patient, such as in the chest of the patient, so as to provide ample space for a relatively large power supply 506. In this manner, the cochlear implant system 100 may be used for relatively long periods of time without recharging or replacing the power supply 506. However, it will be recognized that the implantable power module 502 may be implanted within any other suitable region of the patient, including within the head and/or neck regions, as may serve a particular application.

The implantable power module 502 may include a housing 504 configured to hermetically enclose one or more components of the cochlear implant system 100. For example, the housing 504 shown in FIG. 5 is configured to hermetically enclose power supply 506 and recharge circuitry 508. In some examples, housing 504 may include, but is not limited to, a hermetic encasing configured to prevent entry therein of bodily fluids. The hermetic encasing may be made out of any suitable material including, but not limited to, metal, metal alloys, ceramics, plastics, polymers, and/or combinations thereof. For example, the housing 504 may comprise titanium.

Power supply 506 may include any suitable type of power supply, including, for example, a rechargeable battery. The battery may include any suitable type and/or size of battery as may serve a particular application. For example, the power supply 506 may include an approximately 500 mAh lithium ion battery. A 500 mAh battery may provide power to operate the cochlear implant system 500 for approximately one week under standard operating conditions.

Recharge circuitry 508 may be configured to recharge power supply 506 with power received by power receiver 510. In some examples, recharge circuitry 508 is further configured to prevent over-charging of power supply 506.

Power receiver 510 may be configured to receive power from a power supply located external to the patient (e.g., power supply 424). The power receiver 510 may include any suitable component(s) configured to receive power from an externally located power supply. For example, the power receiver 510 may include a high-Q similar to that described previously.

As shown in FIG. 5, power receiver 510 may be disposed at least partially outside of housing 504. In some examples, the power receiver 510 may be at least partially encased in a protective coating or housing that is distinct from housing 504. For example, the power receiver 510 may be encased in a polymer, such as epoxy, to hermetically seal power receiver 510. In some alternative examples, power receiver 510 may be positioned at least partially within housing 504 and/or integrated into housing 504.

The cochlear implant system may further include a power line 512 configured to electrically couple the implantable power module 502 to the implantable head module 402. In some examples, the power line 512 may include a conductive wire configured to be coupled to the implantable head module 402 via the power input port 414.

As shown in FIG. 5, the use of an implantable power module 502 allows a patient to utilize an external head module 514 that does not include an external power supply. In this manner, the size and/or weight of the external head module 514 may be reduced. However, it will be recognized that in some embodiments, the external head module 514 may include a secondary power supply that is used in conjunction with and/or as a backup for the implantable power supply 506.

Figure 6:
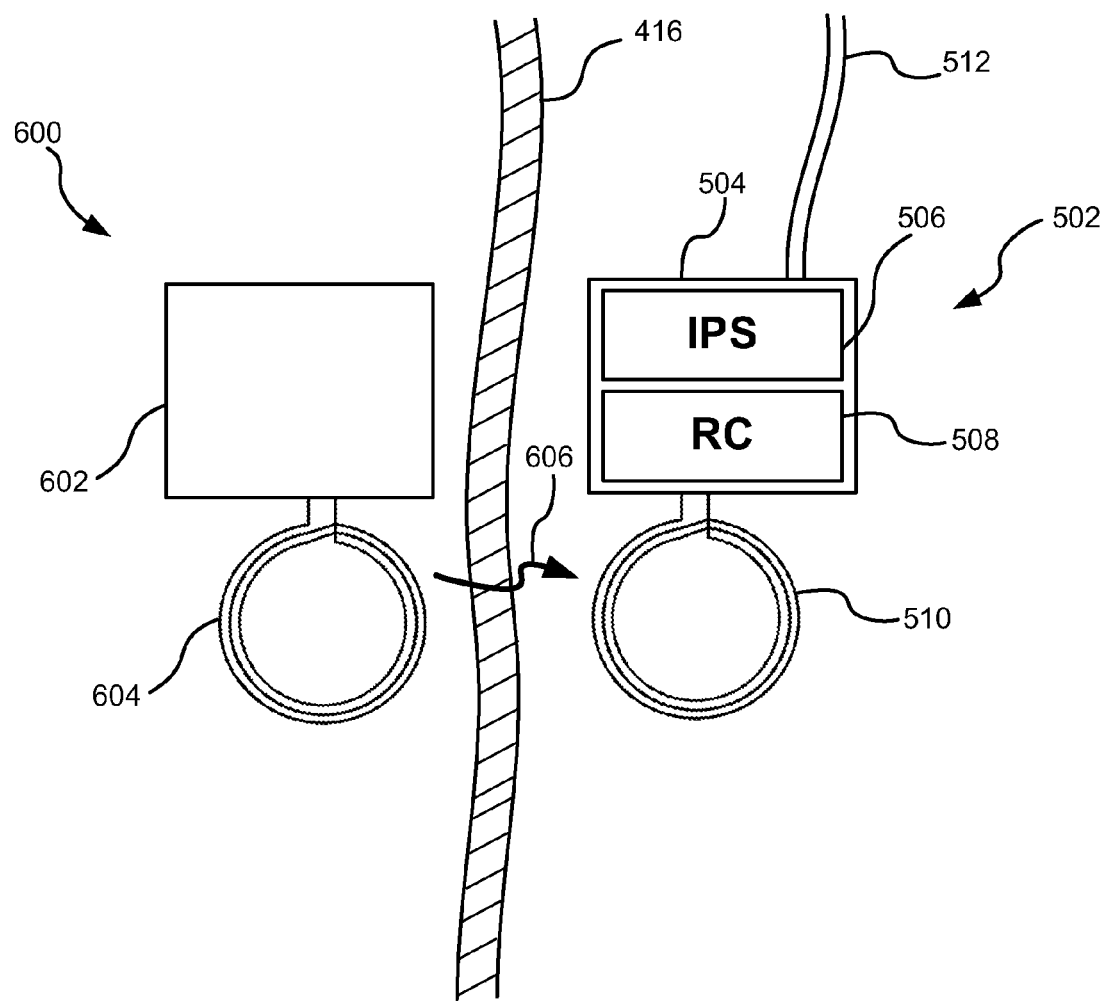
FIG. 6 illustrates an exemplary configuration of a cochlear implant system according to principles described herein.

As mentioned, power receiver 510 may be configured to receive power from a power supply located external to the patient. FIG. 6 illustrates an exemplary configuration wherein an external recharge module 600 is located external to a patient and configured to provide power to power receiver 510. The external recharge module 600 may include any type of power supply as may serve a particular application. For example, the external recharge module 600 may include a housing 602 configured to house a battery, such as a rechargeable lithium ion battery, a transformer, one or more capacitors, and/or any other type of power supply. Additionally or alternatively, the external recharge module 600 may be configured to be directly connected to an electrical source, such as an electrical outlet, such that the external recharge module 600 transfers power from the electrical outlet to the implantable power module 502.

The external recharge module 600 may further include a power transmitter 604, such as a high-Q coil or other suitable power transmitter 604. The power transmitter 604 may be disposed outside the housing 602, as shown in FIG. 6. Alternatively, the power transmitter 604 may be disposed at least partially within and/or integrated into housing 602. Power transmitter 604 may be positioned such that it may transmit power through skin 416 to power receiver 510 via power link 606 when the patient desires to recharge the implanted power supply 504.

Figure 7:
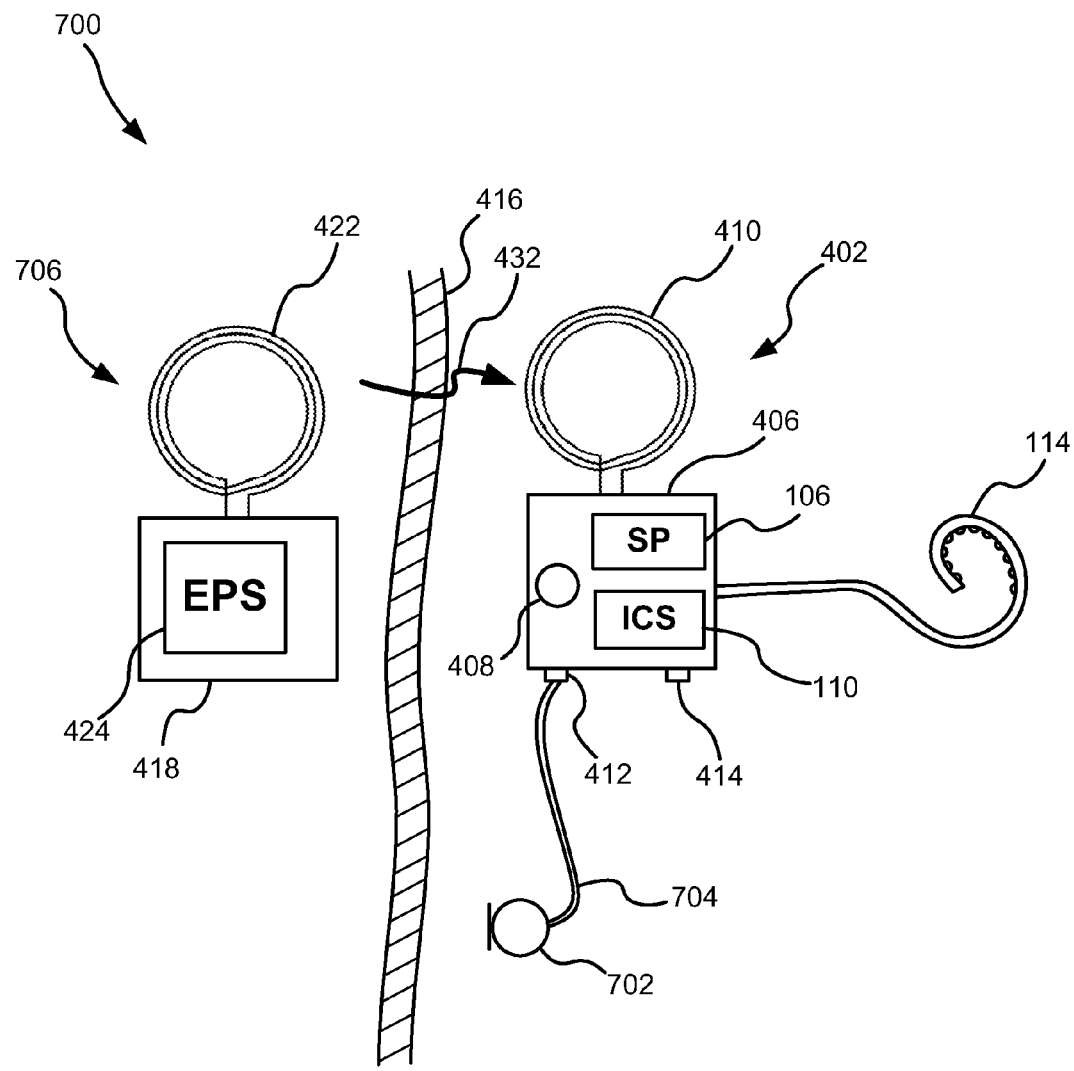
FIG. 7 illustrates an exemplary configuration of a cochlear implant system according to principles described herein.

FIG. 7 illustrates another exemplary modular configuration 700 of cochlear implant system 100. As shown in FIG. 7, configuration 700 includes a microphone 702 configured to be implanted within the patient. The implantable microphone 702 may be positioned within the patient at any suitable location, such as a location within the head region of the patient. The implantable microphone 702 may include a relatively high sensitivity microphone capable of detecting sounds from the environment external to the patient.

Configuration 700 may further include a communication line 704 configured to electrically couple the implantable microphone 702 to the implantable head module 402 via the audio input port 412. By implanting the microphone 702, an external headpiece may not have to be worn by the patient during daily use. When it is desirable to recharge the implanted power supply, an external head module 706 containing only the external power supply 424 and power transmitter 422 may be worn or otherwise positioned near the power receiver 410.

Figure 8:
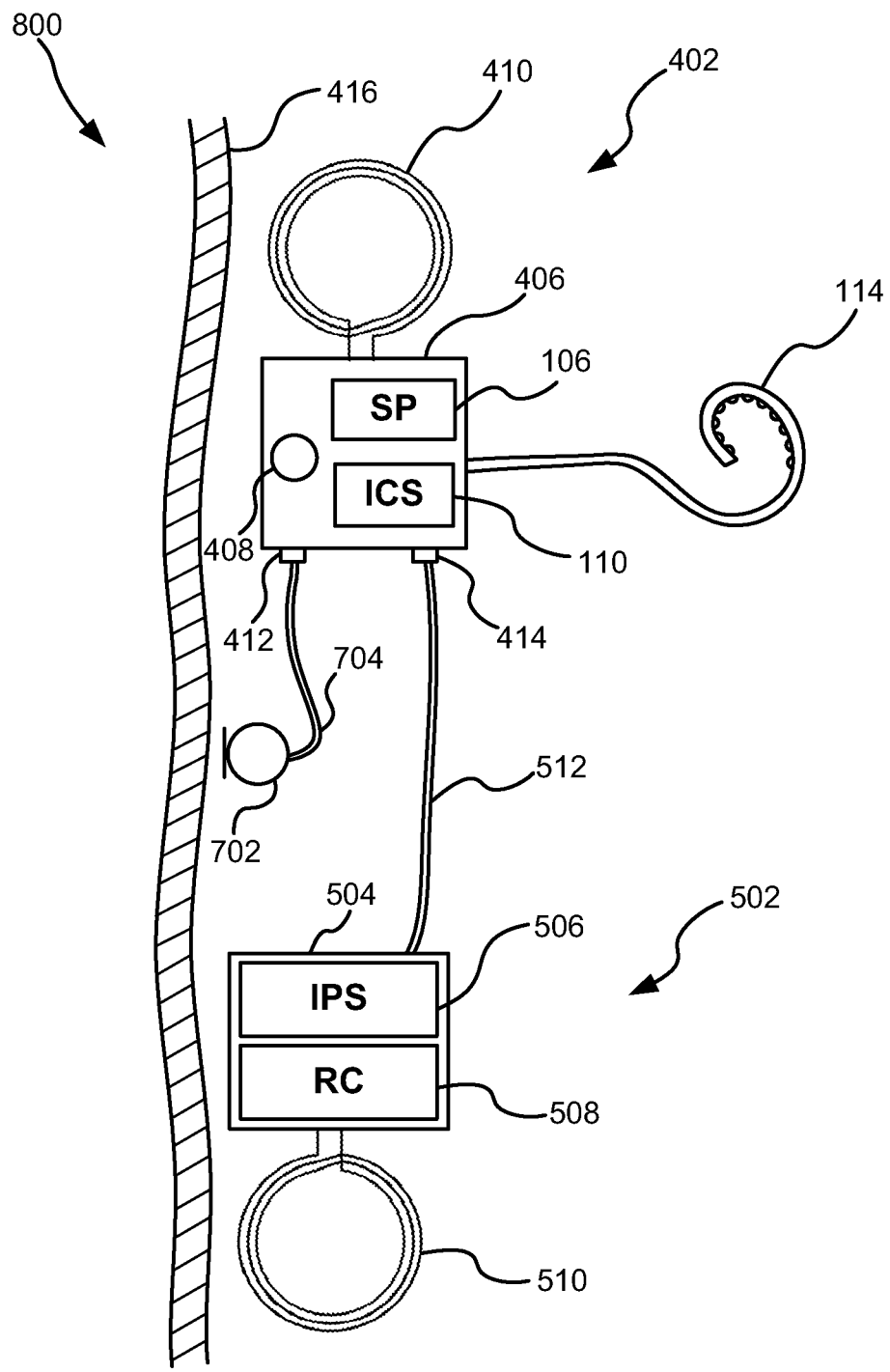
FIG. 8 illustrates an exemplary configuration of a cochlear implant system according to principles described herein.

FIG. 8 illustrates a modular configuration 800 of cochlear implant system 100 that is fully implantable. As shown in FIG. 8, all of the components of the cochlear implant system 100 are fully implanted within a patient. Accordingly, no external head module is required to receive an audio signal or to provide power to the internal components of the cochlear implant system 100.

The configuration 800 shown in FIG. 8 may enable the patient to utilize a cochlear implant system 100 without wearing external components. Accordingly, the added weight and inconvenience to the patient due to external components may be obviated. Additionally, the configuration 800 of FIG. 8 may be aesthetically appealing to many patients due to the elimination of visible external components.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A cochlear implant system comprising:
an implantable head module configured to be implanted within a head of a patient, the implantable head module comprising
a cochlear stimulator configured to be coupled to an electrode lead, the electrode lead comprising one or more electrodes configured to be in communication with one or more stimulation sites within the patient,
a signal receiver configured to receive a telemetry signal representative of an audio signal from a signal transmitter located external to the patient,
a sound processor configured to process the telemetry signal and direct the cochlear stimulator to generate and apply electrical stimulation representative of the audio signal to the one or more stimulation sites via the electrode lead; and
an implantable power module separate from and communicatively coupled to the implantable head module and comprising
a rechargeable battery configured to produce power for operating the implantable head module, and
a power receiver configured to receive power for recharging the rechargeable battery directly from a power transmitter located external to the patient.

2. The cochlear implant system of claim 1, wherein the signal receiver comprises a radio-frequency induction coil.

3. The cochlear implant system of claim 1, wherein the power receiver comprises a high-Q induction coil.

4. The cochlear implant system of claim 1, wherein the implantable head module further comprises an audio input port configured to receive an electrical signal representative of another audio signal from an implantable microphone.

5. The cochlear implant system of claim 1, wherein the implantable head module further comprises a power input port configured to receive power for operating the implantable head module from the implantable power module.

6. The cochlear implant system of claim 1, wherein the implantable power receiver comprises a high-Q induction coil.

7. The cochlear implant system of claim 1, wherein the implantable power module is configured to be implanted within a thoracic region of the patient.

8. The cochlear implant system of claim 7, further comprising a power line configured to electrically couple the implantable power module to the implantable head module.

9. The cochlear implant system of claim 1, further comprising an external head module configured to be positioned external to the patient and communicatively coupled to the implantable head module, the external head module comprising an external microphone for receiving the audio signal.

10. The cochlear implant system of claim 9, wherein the external head module comprises the signal transmitter.

11. The cochlear implant system of claim 9, wherein the external head module comprises the power transmitter.

12. The cochlear implant system of claim 1, wherein the implantable head module further comprises an additional power receiver configured to receive power for operating the implantable head module from the power transmitter located external to the patient.

13. A cochlear implant system comprising:
an implantable head module configured to be implanted within a head of a patient, the implantable head module comprising
a cochlear stimulator configured to be coupled to an electrode lead, the electrode lead comprising one or more electrodes configured to be in communication with one or more stimulation sites within the patient,
a signal receiver configured to receive a telemetry signal representative of an audio signal from a signal transmitter located external to the patient,
a sound processor configured to process the telemetry signal and direct the cochlear stimulator to generate and apply electrical stimulation representative of the audio signal to the one or more stimulation sites via the electrode lead, and
a first power receiver configured to receive power for operating the implantable head module from a power transmitter located external to the patient, and
an implantable power module separate from and communicatively coupled to the implantable head module and comprising
a rechargeable battery configured to produce power for operating the implantable head module, and
a second power receiver configured to receive power for recharging the rechargeable battery directly from a power transmitter located external to the patient;
wherein the implantable head module is configured to selectively operate using power received by the first power receiver and the second power receiver.

14. The cochlear implant system of claim 13, wherein the implantable head module further comprises an audio input port configured to receive an electrical signal representative of another audio signal from an implantable microphone.

* * * * *